United States Patent [19]

Zupanick et al.

[11] Patent Number: 4,865,424

[45] Date of Patent: Sep. 12, 1989

[54] OPTICAL DEVICE WITH ADJUSTING MEANS

[75] Inventors: Joseph E. Zupanick, Richardson; Carl D. McBride, Dallas, both of Tex.

[73] Assignee: Atlantic Richfield Company, Los Angeles, Calif.

[21] Appl. No.: 509,682

[22] Filed: Jun. 30, 1983

[51] Int. Cl.$^4$ .......................... G02B 7/00; G02B 7/24; G02B 5/26; G02B 5/28

[52] U.S. Cl. ................................ 350/321; 350/318; 350/484; 350/588; 356/317

[58] Field of Search ............... 350/484, 568, 537, 567, 350/540, 543, 541, 318, 569, 626, 618, 632, 486, 484, 321; 356/317

[56] References Cited

U.S. PATENT DOCUMENTS 3,840,284 10/1974 Rand .................................. 350/568
4,123,148 10/1978 Laird .................................. 350/618

Primary Examiner—Jon W. Henry
Attorney, Agent, or Firm—James H. Phillips; Michael E. Martin

[57] ABSTRACT

Apparatus is provided to sense and measure solar-induced luminescence, as well as reflectance, within the field of view of a target window for receiving a composite ray of light from the target. A first filter within the path of the composite ray of light transmits a first narrowband component thereof, including a predetermined Fraunhofer Line frequency, to a first sensor. A second narrowband component thereof, proximate the Fraunhofer Line frequency, is directed to a second sensor such that ratios of the electromagnetic energy impinging, respectively, on the first and second sensors may be determined. A removable filter tray carrying the narrowband filters and fine tuning means is employed to facilitate the selection of the predetermined Fraunhofer Line frequency.

5 Claims, 4 Drawing Sheets

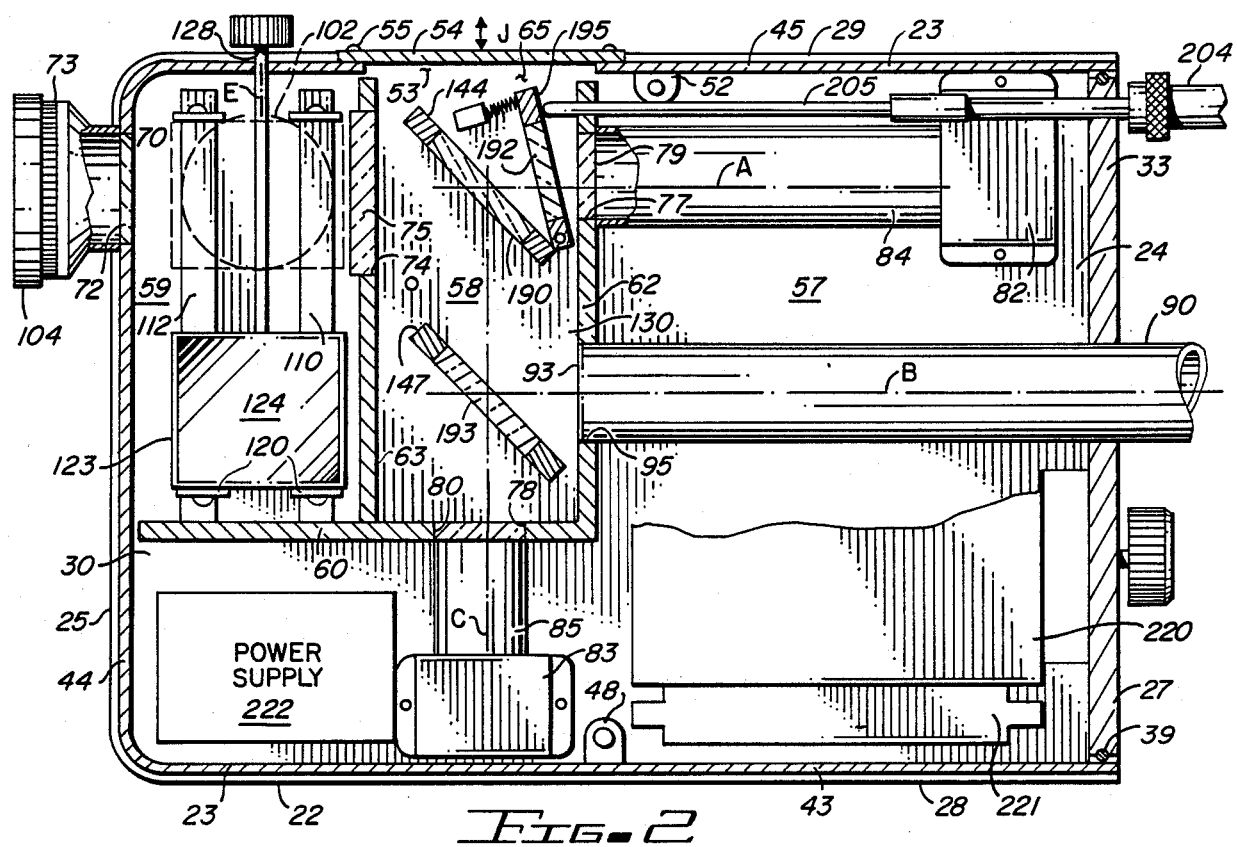
Fig. 2
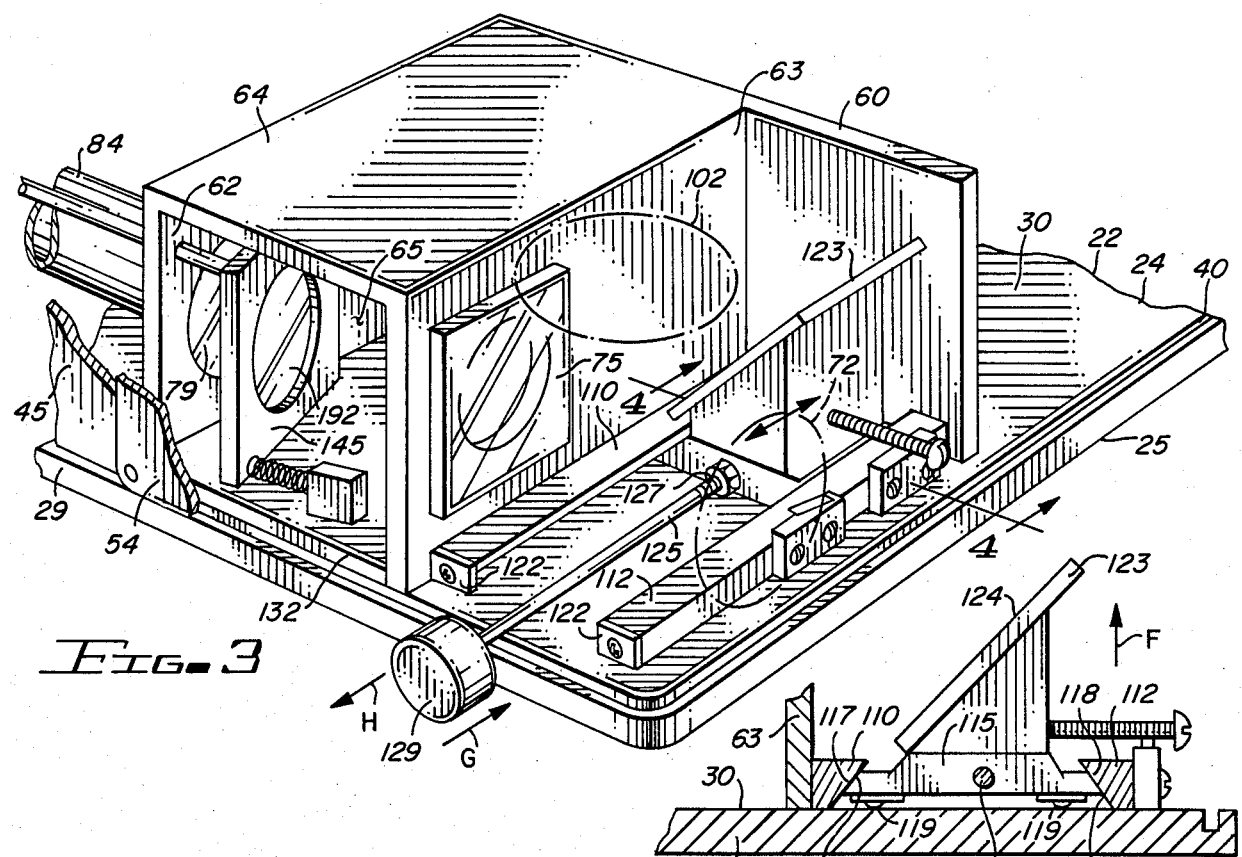
Fig. 3
Fig. 4

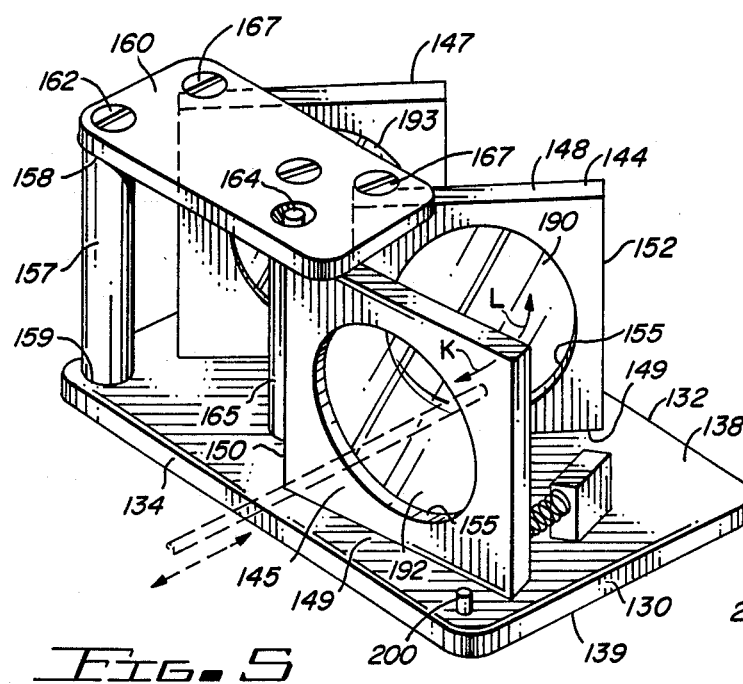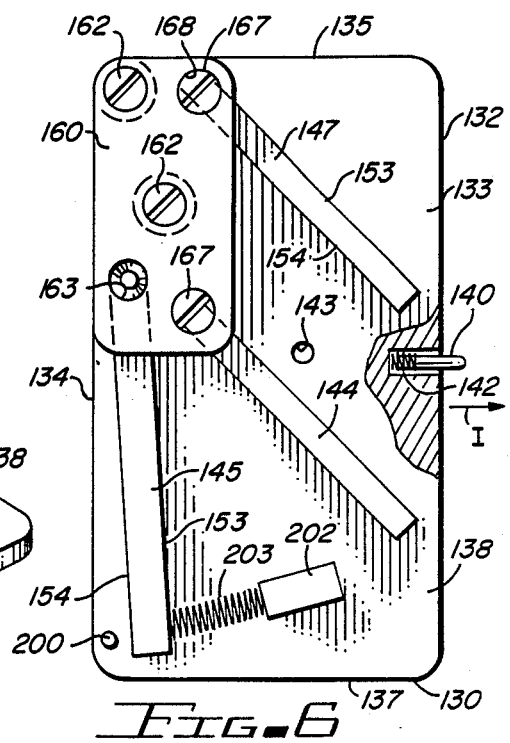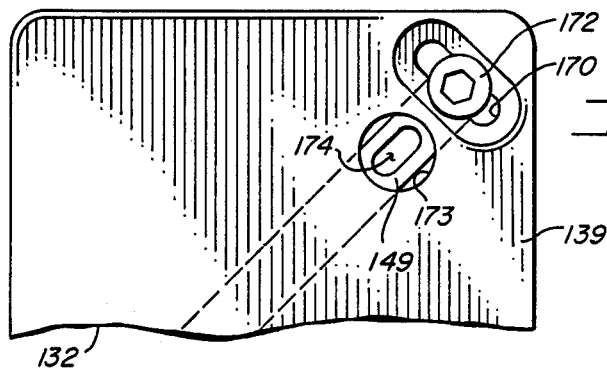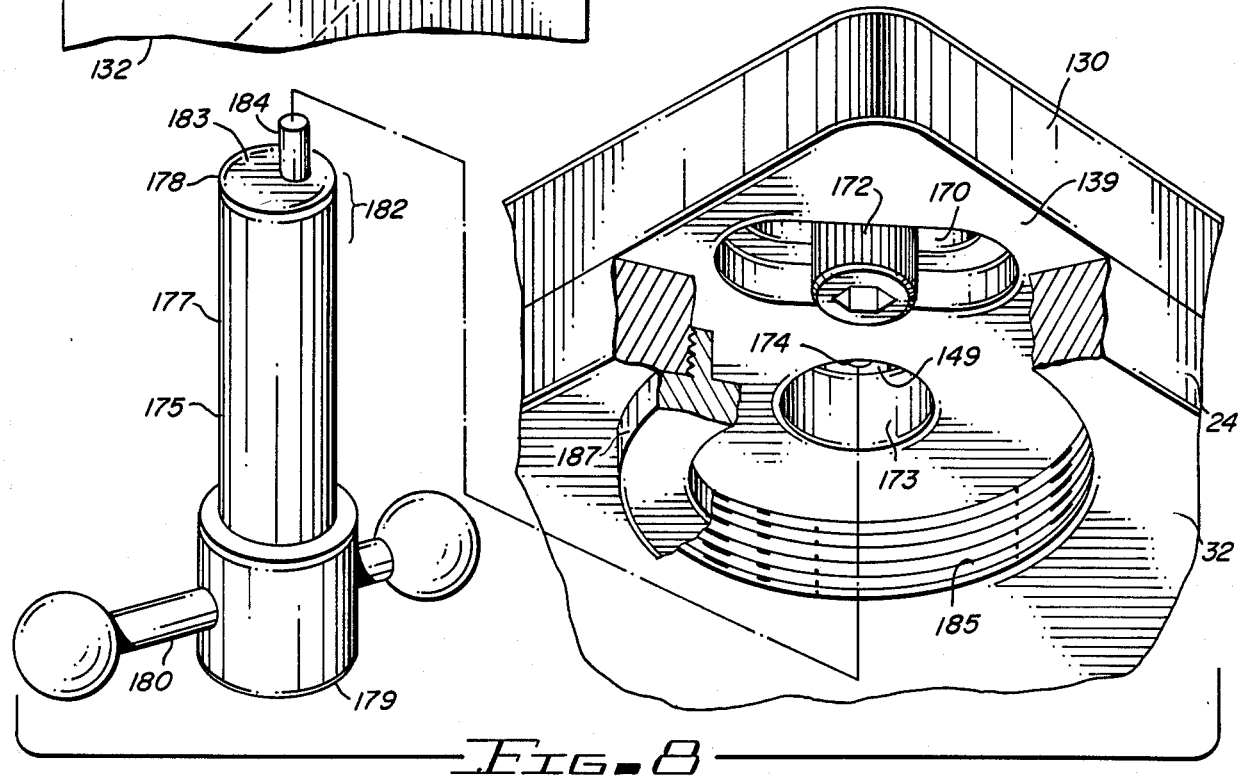

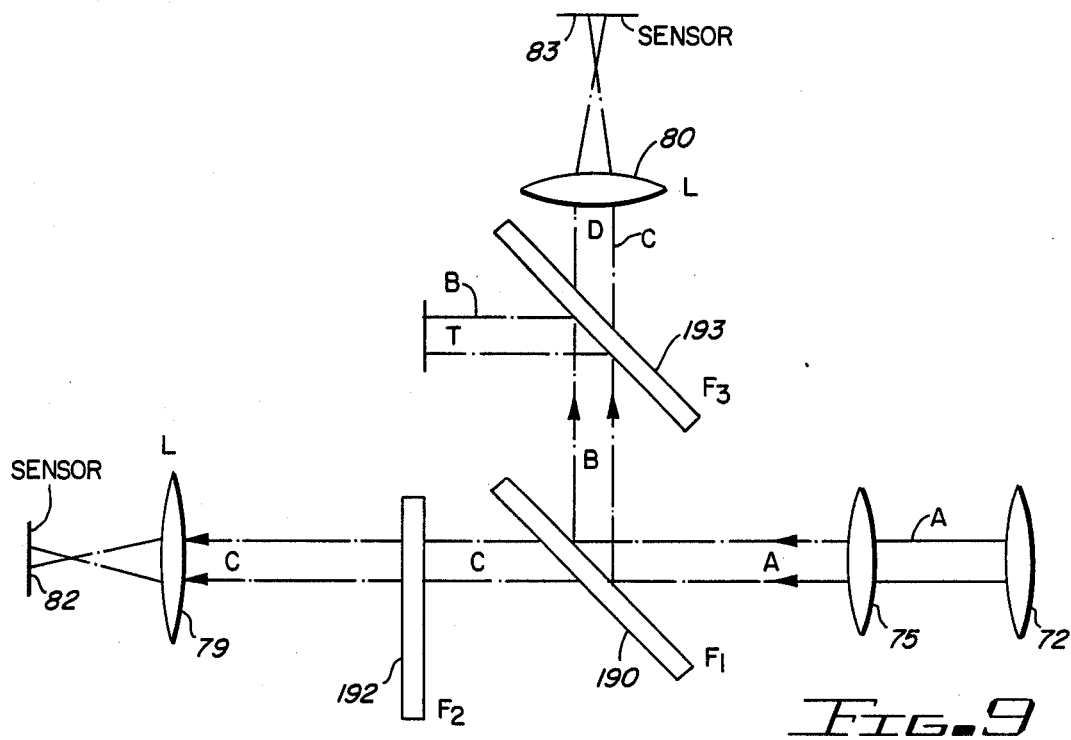
FIG. 9
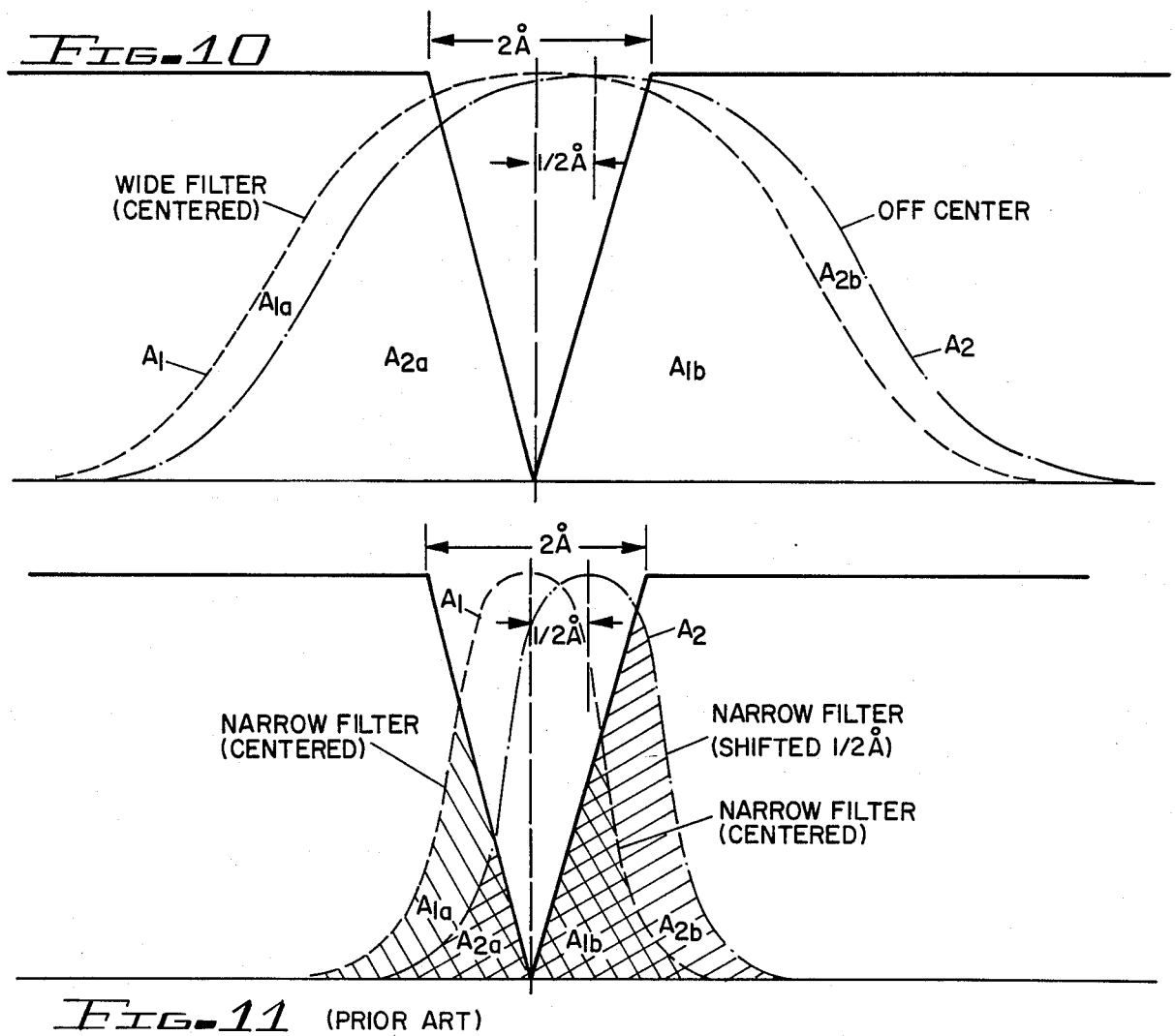
FIG. 10
FIG. 11 (PRIOR ART)

OPTICAL DEVICE WITH ADJUSTING MEANS

BACKGROUND OF THE INVENTION

1. Field of the Invention

This invention relates to light sensing instruments.

More particularly, the present invention relates to means and method for sensing and measuring luminescence and reflectance.

In a further and more specific aspect, the instant invention concerns a portable device for sensing and measuring luminescence and reflectance of selected targets in the presence of sunlight.

2. Prior Art

It is generally well recognized that a ray or line of light is actually a continuously moving stream of energy particles termed "photons". The photons are emitted from the light source in pulses. Traveling at incomparable speed and being almost immeasurably diminutive, a stream of photons assumes wave-like characteristics.

Analogous to other wave forms, light has the properties of speed, frequency and wavelength. The speed is a constant, being the speed of light. Both frequency and wavelength are variable. Accordingly, properties for any type of light can be delineated by the formula:

$$c = f \times (\lambda)$$

where:
- c = speed of light
- f = frequency; and
- $\lambda$ = wavelength.

Types of light are generally referenced with respect to the corresponding wavelength. The known types of light are juxtaposed along a continuum ranging from the short gamma rays, having wavelengths in the range of $1 \times 10^{-4}$ Angstroms, to the long radio waves, having wavelengths in the range of $1 \times 10^{17}$ Å. Apparatus for producing light within a specific narrow band, such as an X-ray machine, are well known. The sun emits the full spectrum of light.

However, it is now recognized that light from the sun is not uniformly intense along the wavelength gradient. Throughout the spectrum are instances of the absence or diminishing of light, causing a dip in a plot of spectral energy against frequency. A number of these dips are known as Fraunhofer Lines, and numerous Fraunhofer Lines, or absorption bands, can be found along the light spectrum. As is well known in the art, Fraunhofer Lines result from selective absorption of narrow light frequencies by gases surrounding the sun.

Light falling upon a body is either reflected or absorbed. Photons striking a surface and not absorbed, leave the surface at a substantially identical wavelength. This photon behavior is ordinarily called "reflection". Reflected light emulates the source light. Thus, in the case of reflected sunlight, the Fraunhofer absorption bands are present.

The behavior of a photon being absorbed by material and causing the reemittance of light is referred to as "luminescence". Luminescent light is at another, usually longer wavelength than the excitation source light and does not contain the Fraunhofer Lines or dips. Solar-stimulated luminescence is a naturally occurring phenomenon in various sources, such as mineral deposits and vegetation.

It is well known that insight into nature and composition of a luminescent substance can be achieved by inspection of the emanant light. This is readily accomplished by employing a spectrophotometer under laboratory conditions. Field exploration for luminescence materials has been carried out in the past on dark nights by using ultraviolet lamps to stimulate luminescence and the human eye as the detector. The severe limitations of such nighttime field efforts are notoriously well known to exploration geologists.

Although sunlight excites and stimulates luminescence in a substance upon which it shines, sunlight simultaneously masks the relatively faint luminescence of the substance with a large energy return from reflectance. Thus, sensing solar stimulated luminescence is a formidable undertaking which, however, may be accomplished by taking advantage of the presence of the previously mentioned Fraunhofer Lines in the spectrum of sunlight impinging on the object being observed.

Sunlight generally shows a very sharp Fraunhofer Line in a measurement of light intensity, whereas a luminescent substance shows no Fraunhofer Line in its light intensity in the same spectrum range. Yet, the combination of the luminescent radiation of the substance and reflected sunlight will yield a measurement of intensity of a level nearly equal to that of direct sunlight with a greatly reduced Fraunhofer Line. Individual substances radiate in differing amounts, thereby reducing Fraunhofer Line of reflected sunlight in difference degrees. Charts of the various luminescent radiations of different substances are readily available or may be experimentally determined. Accordingly, by measuring the intensity of direct sunlight within a given waveband and its corresponding Fraunhofer Line, and comparing it to the intensity of reflected sunlight from a luminescent target with its altered Fraunhofer Line within the same waveband, it is possible to calculate the change in the dip attributable to the luminescent radiation of the target and hence the luminescence. Subsequent comparision to a chart of known values will identify or give insight into the target substance.

A device for this purpose is set forth in U.S. Pat. No. 3,598,994 upon which is based the famous Fraunhofer Line Discriminator used for some years by the U.S. Geological Survey at Flagstaff, Arizona. The subject device simultaneously takes a reading of direct sunlight within a narrow waveband and its spectrally corresponding immediately adjacent Fraunhofer Line, and a reading of reflected sunlight and luminescent radiation of a substance and that corresponding Fraunhofer Line within the same waveband as the reading for direct sunlight.

The prior art device, requiring simultaneous readings of direct sunlight and reflected light, necessitates a plurality of lenses, filters and prism in an arrangement requiring an inordinate amount of space, making it impossible for a user to carry the unit in one's hands. Additionally, the number and type of lenses and prisms make the device very heavy and excessively expensive to produce. Further, the Fabry-Perot type filter, as used in the prior art device, operate properly only within an exceedingly narrow temperature range, thereby mandating an adjunct temperature control unit adding materially to the weight, bulk and cumbersomeness. It is also noted that the device is not suitable for rapid, convenient adaptation for operation in multiple selected wavebands.

It would be highly advantageous, therefore, to remedy the foregoing and other deficiencies inherent in the prior art.

Accordingly, it is an object of the present invention to provide improved means and method for sensing and measuring luminescence emanating from a selected target.

Another object of the invention is the provision of luminescence sensor of substantially reduced weight and bulk rendering the sensor hand portable.

And another object of this invention is to provide a luminescence sensor which is relatively insensitive to temperature deviations within a range as normally occuring throughout a typical day.

Yet another object of the invention is the provision of a portable luminescence sensor having a readily changeable optical assembly to accommodate a selected luminescent target.

Still a further object of the invention is the provision of a portable luminescence sensor which is comparatively simple and is inexpensive to fabricate.

Yet a further object of this invention is to provide a portable luminescence sensor which is relatively unencumbered and substantially maintenance free.

And a further object of the invention is the provision of a device of the foregoing character which may be assembled in a manually portable package.

SUMMARY OF THE INVENTION

Briefly, to achieve the desired objects of the instant invention, in accordance with a preferred embodiment thereof, first provided is a body having a target window for receiving a composite ray of light emanating from a luminescent target along a first optical path. A first filter aligned along the first optical path transmits a first component of said composite ray of light, including a selected waveband having an intermediate selected Fraunhofer Line, and redirects the balance of said composite ray of light, along a second optical path.

The first component is received by a first sensor which provides an indication of the energy level. Similarly, the second component of light is received by a second sensor. Means are provided to convert the output of the sensor to sensible indicia.

Further provided is a lens for receiving direct light, such as sunlight, along a third optical path. A diverter, preferably including a reflective surface, is selectively positionable to direct light from said third optical path to travel along said first optical path.

A second filter, aligned along the first optical path, narrows the ray of light from the first filter to a waveband of selected width in the intermediate range of the selected Fraunhofer Line. A third filter aligned along the second optical path narrows the light from the first filter to a predetermined waveband offset from said Fraunhofer Line by a selected frequency difference. Each filter is selectively angularly adjustable relative the respective optical path. Tuning means for calibrated adjustment are further associated with the second filter.

In accordance with a further embodiment, there is provided a viewing scope for observing the target through the target window. The filters may be carried by a tray interchangably receivable within said body. Optical filters may also be provided to block the entrance of light having wavelengths lesser or greater than that of visible light.

BRIEF DESCRIPTION OF THE DRAWINGS

The foregoing and further and more specific objects and advantages of the instant invention will become readily apparent to those skilled in the art from the following detailed description of a preferred embodiment thereof, taken in conjunction with the drawing in which:

FIG. 2 is a horizontal sectional view taken along the line 2—2 of FIG. 1.

FIG. 3 is an enlarged fragmentary perspective view of the lens and filtering portion of the device seen in FIG. 2;

FIG. 4 is a fragmentary vertical sectional view taken along the line 4—4 of FIG. 3;

FIG. 5 is an enlarged perspective view of an interchangeable filter tray assembly usable in the instrument;

FIG. 6 is a top plan view of the filter tray assembly seen in FIG. 5, a portion thereof being broken away to reveal additional detail;

FIG. 7 is an enlarged bottom plan view of a fragmentary portion of the filter tray assembly of FIG. 5, especially illustrating a preferred means for adjusting the filter holders;

FIG. 8 is further enlarged perspective view of the portion of the filter tray assembly seen in FIG. 7, as it would appear when assembled with the instrument of FIG. 1, the instrument being shown in fragmentary perspective, and further illustrating an adjusting tool for use in combination therewith;

FIG. 9 is a diagramatic representation of the optical paths within the device of FIG. 1;

FIG. 10 is a graphic representation of sunlight intensity, chosen in a selected band to include a Fraunhofer Line, and having a corresponding band as viewed by the instrument of the instant invention superimposed thereon; and FIG. 11 is an illustration, generally corresponding to the illustration of FIG. 10, except having a prior art view of luminescence light superimposed thereon.

DESCRIPTION OF THE PREFERRED EMBODIMENT

Figure 1:
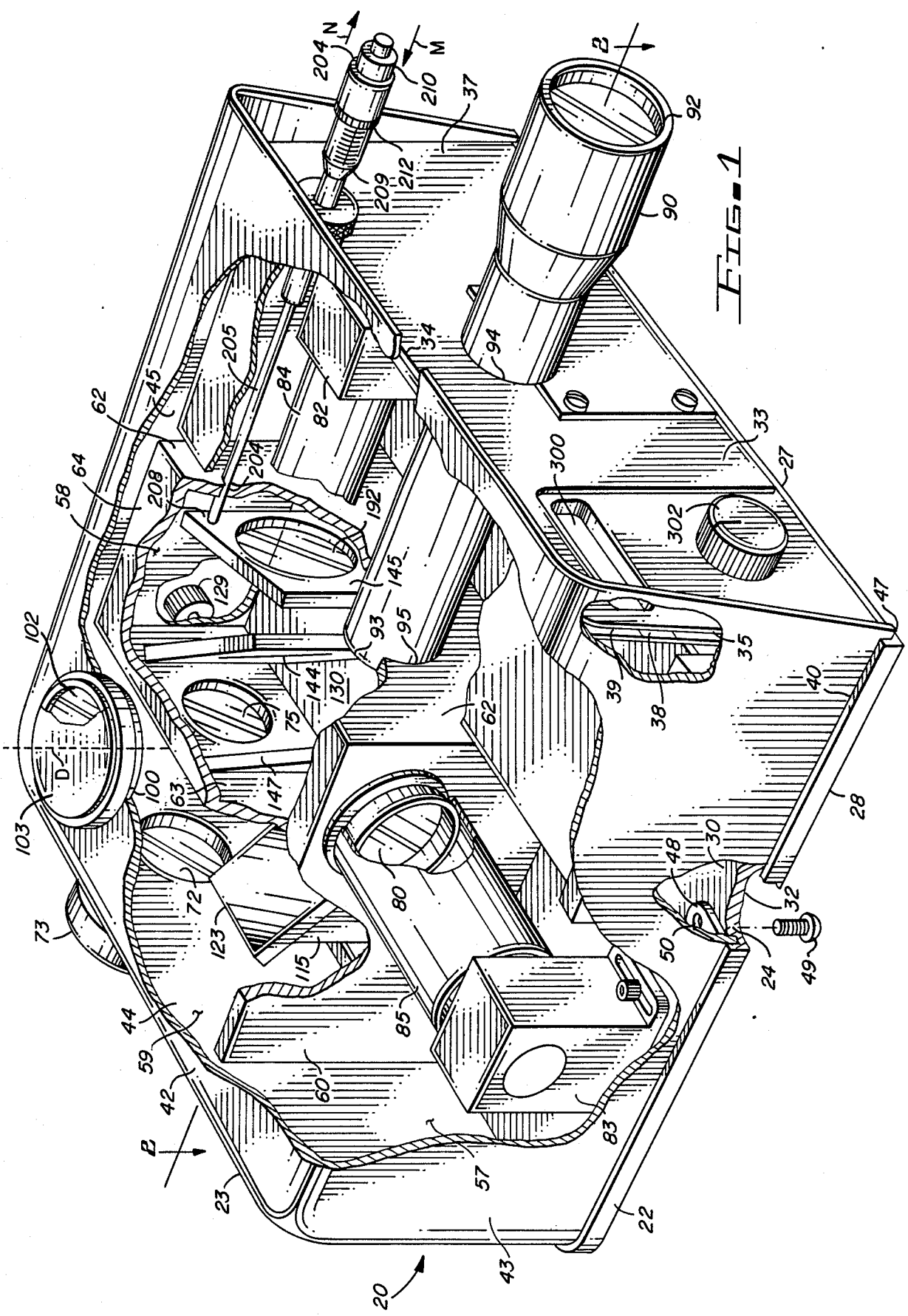
FIG. 1 is a perspective view, partially broken away for purposes of illustration, of a portable luminescence sensing and measuring instrument embodying the principles of the instant invention.

A portable luminescence sensor, embodying the principles of the instant invention, will now be described with reference to the drawing. First, the structure of a preferred embodiment will be described in detail. Subsequently, the operation and function will be delineated. In the ensuing narrative, like reference characters will denote corresponding elements throughout the several views.

Structure

Attention is first directed to FIG. 1, which illustrates a preferred embodiment of a portable luminescence sensor constructed in accordance with the teachings of the instant invention. The body of the device is in the form of a case or housing, generally designated by the reference character 20, having a base structure 22 and a removable cover structure 23. With further reference to FIG. 2, it is seen that the primary support member of base structure 22 is generally rectangular base plate 24 having forward edge 25, rearward edge 27, left edge 28, right edge 29, and top and bottom surface 30 and 32, respectively. (The terms forward, rearward, left, and right are used herein for purposes of orientation in the ensuing description. Similarly, edges 28 and 29 are considered to be longitudinal while edges 25 and 27 are considered to be lateral. Such terms are set forth for purposes of convenience and not limitation).

Rear panel 33, having upper edge 34, upright left edge 35 and upright edge 37, projects upwardly from rear edge 27 of base plate 24. Seal groove 38, carrying seal 39, extends continuously along edges 34, 35, and 37. Cover receiving groove 40, formed in top surface 30 of base plate 24, extends continuously at a location speed slightly inboard from edges 25, 28, and 29.

Cover structure 23, being somewhat in the form of an inverted box, includes generally rectangular top panel 42, having integral, depending, continuous left, forward, and right side panels 43, 44, and 45, respectively. The several side panels terminate the continuous lower edge 47 which, in the assembled configuration, is received in groove 40. In order to provide a light impervious union between base structure 22 and cover structure 23, the continuous under surface of top panel 42 and side panels 43 and 45 are received in sealing engagement against seal 39.

A tab 48, projecting inwardly from side panel 43, is positioned to rest upon top surface 30 of base plate 24 when edge 47 is fully received within groove 40. Screw 49, received through a clearance sized opening (not illustrated) in base plate 24, threadedly engages aperture 50 in tab 48 for detachable securement of cover structure 23 to base structure 22 in accordance with conventional technique. A similar tab 52 for a like purpose is seen projecting inwardly from side 45 in FIG. 2. As will be apparent to those skilled in the art, additional attachment structures may be periodically spaced throughout the arrangement. Similarly, while screw 49 has been specifically illustrated as a machine screw, it will be appreciated that other commercially available fastening elements may be readily substituted.

An opening 53, the purpose of which will be discussed presently, is formed through right side panel 45. Cover plate 54, removably secured to the exterior of right side panel 45, as by sheet metal screws 55, normally closes opening 53. To insure a light impervious assembly, a flat gasket-type seal may reside between cover plate 54 and right side panel 55.

The interior of case 20 is partitioned into first, second and third compartments 57, 58, and 59, respectively, by an arrangement of panels extending upwardly from the top surface 30 of base plate 24. First panel 60, intermediate and parallel to left and right edges, 28 and 29, respectively, extends longitudinally from proximate forward edge 25 to an intermediate terminal location. Second panel 62 is transverse, extending between first panel 60 and right edge 29. Third panel 63 is also transverse, extending between first panel 60 and right edge 29, at an intermediate location between second panel 62 and forward edge 25. Cover panel 64, having respective edges adjoining the panels 60, 62, and 63, overlays compartment 58. Accordingly, compartment 58 has an open end 65 in substantial alignment with opening 53 through right side panel 45 of cover structure 23.

The housing 20 may be fabricated of various materials by respectively suitable manufacturing techniques. For example, case 20 may be structured of metal, such as aluminum, by appropriate stamping techniques. Similarly, the housing may be molded of a plastic material. The several components may be integrally formed, or alternately, individually shaped and assembled by employing fastening devices or adhesives compatible with the selected material. Such devices are well known in the art as are commercially available cases which may be modified for the immediate purpose.

In accordance with the immediately preferred embodiment of the instant invention, the several optical elements are lined along prescribed interrelated axes. For purposes of illustration and reference during the ensuing description, these axes are designated as first, second, third, and fourth, as represented by the broken lines indicated by the alphabetic reference characters A, B, C, and D, respectively. As shown in FIG. 2, the axes represented by the reference characters A, B and C, line in a single plane with the former two extending in longitudinal parallelism. The latter is laterally extending, being a perpendicular bisector of the former. The axis represented by the reference character D, being perpendicular to the described plane, intersects the axis represented by the reference character A. Each of the designated axes is considered the longitudinal axis of an optical path along which a ray of light moves.

An opening 70 is formed through forward side panel 44 of cover structure 23. An ultra-violet cutoff optical filter 72, of a standard commercially available type as will be known to those skilled in the art, is fixed in opening 70 by any suitable lens mounting means, such as a suitable adhesive. Tubular shield 73 projects forwardly from panel 44. For inclusive reference, opening 70, filter 72, and shield 73, having axis A as the common center, is termed the target window.

Opening 74, extending through third panel 63, carries infra-red cutoff optical filter 75. Filter 75, secured within opening 74 by conventional means in alignment with axis A, is likewise of standard commercial manufacture.

Aperture 77 is formed through second panel 62. Aperture 78 is similarly formed through first panel 60. Objective lenses 79 and 80 are mounted within apertures 77 and 78, respectively. Lens 79 is aligned along Axis A. Lens 80 is aligned along axis C. Each of the lens 79, 80 is of the familiar configuration generally referred to as focusing lens. Hereinafter, lens 79 will be referred to as first objective lens while lens 80 will be referred to as second objective lens.

First sensor 82, residing in compartment 57, is aligned along axis A. A second sensor 83, also residing within compartment 57, is aligned along axis C. Representative of the sensor 82 and 83, is blue enhanced photovoltaic silicon device manufactured by Silicon Detector Corporation, under the Identification No. sd-200-12-12-241. As supplied by the manufacturer, the device is provided with outwardly directed flanges at the base for attachment to base plate 24 by conventional screws. Tubular element 84 provides light tight communication between lens 79 and sensor 82. Similarly, tubular element 85 provides a light impervious path between lens 80 and sensor 83.

Viewing scope 90, having ocular end 92 and objective end 93, extends through openings 94 and 95 in rear panel 33 and second panel 62, respectively. Field end 93 terminates in the approximate plane of panel 62. Ocular end 92 is spaced rearwardly of panel 33. Viewing scope 90 may be of any commercially available type conventionally used as a sight for rifles or other firearms. Although a relatively low magnification in the range of 1x to 3x power is preferred, scopes of greater power or variable power are contemplated.

A conventional annular lens holder 100 is secured within an appropriate opening through top panel 42 of cover structure 23. Diffusing plate 102 is carried by lens holder 100. Lens holder 100 projects upwardly from top panel 42 and removably receives lens cover 103 in accordance with standard practice. As a preferred standard, diffusing plate 102 is free from florescence with a twenty percent light transmission as will be readily understood by those in the lens making art. Plate 102, the relative position of which is shown in broken outline in FIGS. 2 and 3, is aligned along axis D. The relative positioning of optical filter 72 is also seen in broken outline in FIG. 3. A second lens cover 104, generally similar to lens cover 103, is detachably securable to tublar shield 73.

Diverter means for selectively and optionally receiving light entering case 20 through lens 102 along the optical path represented by the broken line D and redirecting the light along the optical path represented by the broken line A in a direction toward sensor 82 resides within compartment 59. As more clearly viewed in FIGS. 3 and 4, the immediately preferred diverter means includes a pair of spaced apart parallel ways 110 and 112. The ways reside along a transverse axis, represented by the broken line E which, when observed in plan view, is perpendicular to the axis represented by the broken line A. Being generally triangular in cross-section, and secured to the top surface 30 of base plate 24 by any convention expedience, ways 110 and 112 carry elongate guide surfaces 113 and 114, respectively. Guide surfaces 113 and 114 are in opposition and appear in cross-section as being mutually, downwardly, outwardly divergent.

Slide 115 is disposed between ways 110 and 112. Carried by slide 115 are opposed outwardly, downwardly, divergent contact surfaces 117 and 118 which are matingly received against the guide surfaces 113 and 114, respectively. Spring loaded plungers 119, of conventional commercially available configurations, carried by slide 115, bear against surface 30 of base plate 24, urging slide 115 upwardly in the direction of arrowed line F, maintaining surfaces 117 and 118 in juxtaposition with and bearing against the respective guide surfaces 113 and 114. The travel of slide 115 in either direction along axis E is limited by positive stops. In the immediately preferred embodiment, the stops assume the form of interference tabs 120 carried at the inner end of ways 110 and 112 and interference tabs 122 affixed to the outer end.

Mirror 123, having reflective surface 124, is supported at an oblique angle by slide 115. Operating rod 125 projects from slide 115 parallel to axis E. The fixed end 127, of operating rod 125, is threadedly engaged within slide 115. Free end 128 of operating rod 125 resides external of case 120. Hand knob 129 is carried at free end 128.

Mirror 123, in response to manual manipulation of hand knob 129, is selectively movable in alternate directions along axis E between a first position and a second position. The first position is obtained by applying manual pressure to hand knob 129 in the direction of arrowed line G, correspondingly moving slide 115 against inner stops 120. Movement of hand knob 129 in the direction indicated by arrowed line H, relocates mirror 123 in the second position wherein slide 115 bears against outer stops 122. With mirror 123 in the first position, light entering through filter 72 is free to travel along the axis represented by the arrowed line A, as previously described. With mirror 123 in the second position, the normal optical path of light entering through lens 102 along the axis represented by the broken line D (see FIG. 1) is redirected along the axis represented by the broken line A in a direction toward sensor 82. For optimum operation, it is apparent that the physical center of reflecting surface 124, when in the second position, should reside at the intersection of axes A and D. Further, reflective surface 124 should be oriented at forty-five degrees to each of the associated optical paths.

Equivalent structural configurations for achieving the desired function will readily occur to those skilled in the art. For example, slide 115 may be movable upon spring loaded gibs of traditional design. Various detent means may be substituted for the interference tabs and allow for the removal of slide 115. Similarly, the movement of slide 115 may be in response to a manually rotated or motor driven lead screw.

A filter tray assembly 130, detailedly depicted in the enlarged enhancements of FIGS. 5 and 6, removably resided within compartment 58. Filter tray assembly 130 includes base 132 which, described in reference to the assembed relationship with case 20, includes forward edge 133, rearward edge 134, inner edge 135, outer edge 137, and top and bottom surfaces 138 and 139, respectively. Plunger 140, normally biased in the direction of arrowed line I by compression spring 142 and being of known configuration, projects from forward edge 133. Threaded aperture 143 extends through base 132 between surfaces 138 and 139.

Filter tray assembly 130, along with the associated structure to be subsequently described, is removable and replaceable through opening 53 in right side panel 45 of cover structure 23. The lower portion of the surface of second panel 62 adjacent compartment 58, functions as an alignment surface for receiving rearward edge 134 which serves as a complemental alignment surface thereagainst. Similarly, the third panel 63 adjacent compartment 58 functions as a contact surface for receiving the contact end of plunger 140 thereagainst. Plunger 140 and spring 142 function as biasing means for urging the alignment surfaces into juxtaposition. Accordingly, base 132 is slidable within compartment 58 in selective opposite directions as indicated by the double arrowed line J. In the inward direction, surface 135 abuts first panel 60 to provide stop means. A bolt, receivable through an opening in base plate 24 and threadedly engagable within aperture 143, brings surface 139 of base 132 into contact with top surface 30 of base plate 24 to positionally retain filter tray assembly 130. The opening through base plate 24 and the bolt, although not specifically herein illustrated, are conventional for the intended purpose as will be appreciated by those skilled in the art.

Supported by base 132 are first, second, and third filter holders 144, 145, and 147, respectively. For convenience of manufacture, each filter holder is identical, being generally rectangular and including parallel upper and lower edges 148 and 149, respectively, and parallel upright edges 150 and 152. Also included are opposing faces 153 and 154. An aperture 155 extends through each filter holder between faces 153 and 154.

Each filter holder is pivotally supported in a generally upright position for rotational, angular adjustment. A stand-off post, having upper end 158 and lower end 159, rises substantially perpendicularly from top surface 138 of base 132, proximate the apex of edges 134 and 135. Although not specifically herein illustrated, lower end 159 is secured to base 132 by any conventional known means, such as a bolt extending through base 132 and threadedly engaged within post 157. Support plate 160, cantileveredly extending over at least a portion of each of the filter holders, is secured to the upper end 158 of post 157, as by flat head machine screw 162.

Filter holder 145 is affixed to tray 132 by pivot means including bore 163 extending through support plate 160 and an aligned bore (not illustrated) extending through base 132. Pin 164, carried proximate upright edge 150, subtends edges 148 and 149 and is rotatably journaled within respective bores. In the assembled configuration, as seen in FIG. 2, the axis of rotation of pin 164 is perpendicular to the plane defined by the axes A, B, and C. To prevent binding and insure free rotation of filter holder 154, and auxiliary stand-off post 165 extends between base 132 and plate 160 at a location spaced from stand-off post 157.

A portion of each of the filter holders 144 and 147, adjacent the respective upright edge 150, resides between base 132 and support plate 160. Extending into each filter holder 144 and 147, from the respective top edge 148 and the respective upright edge 150, is a threaded aperture (not specifically illustrated), which receives a respective flat head machine screw 167 extending through an appropriate sized countersunk bore 168 in plate 160.

Filter holders 144 and 147 are secured to base 132 as clearly seen with reference to FIG. 7. An opening 170 is formed through base 132 in alignment with countersunk bore 168. Preferably, opening 170 is elongated in a direction perpendicular to the normal residence direction of lower edge 149 of the respective filter holder. A bolt 172, herein illustrated as a socket head cap screw, extends through opening 170 and is threadedly received within an opening in the respective filter holder aligned with the threaded opening receiving the screw 167. Accordingly, each filter holder 144 and 147 is rotatable about an axis parallel to the axis of pin 164.

As further seen in FIG. 7, a bore 173 extends through base 132 along an axis substantially parallel to the axis of rotation, and spaced from opening 170 in a direction along the normal residence position of the respective filter holder. A slot 174, elongated in a direction parallel to the faces 153 and 154, is formed into the lower edge 149 of each filter holder 144 and 147.

Referring now to FIG. 8, there is seen driver 175, including elongate shank 177, terminating with a working end 178 and handle end 179. T-handle 180 is carried proximate handle end 170. Bearing surface 182, adjacent working end 178, is sized to be matingly and rotatingly received within bore 173. Perpendicular to cylindrical bearing surface 182 and residing at end 178, is flat bearing surface 183 which may be receivable against edge 149 of the respective filter holder 144 or 147. Cylindrical pin 184 projects from bearing surface 183 along an axis spaced from and parallel to the axis of rotation of cylindrical bearing surface 182. Pin 184 is receivable within slot 174 when bearing surface 182 is received within bore 173.

With filter tray assembly 130 positioned within compartment 158, aperture 155 of filter holder 144 resides proximate the intersection of the area represented by the broken lines A and C. Similarly, the aperture 155 of filter holder 147 resides the intersection of the axes represented by the broken lines B and C. The elements described with specific reference to FIGS. 7 and 8 provide adjusting means for rotating the filter holders about an axis of rotation to selective angular positions relative the above mentioned axes. Bolt 172, and optionally screw 167, function as locking means for selectively retaining the respective filter holder at a selected one of the positions.

Slot 174, as will be appreciated by those skilled in the art, is defined by a continuous side wall. Contained within the side wall is a pair of spaced parallel sub-surfaces which serve as camming surfaces. Pin 184 functions as a cam to bear against a selected one of the camming surfaces. In response to rotation of driver 175, with bearing surface 180 matingly received within bore 173, the eccentric pin 184 bears against the side wall of slot 174 to angularly direct the selected filter holder about the respective axis of rotation. Subsequently, bolt 172 is tightened in the usual manner to immovably fix the filter holder at the selected position.

With further reference to FIG. 8, there is seen means for facilitating alignment and adjustment of filter holder 144 and 147 when filter tray assembly 130 is located within compartment 158. A pair of threaded apertures 185 extend through base plate 24. Each aperture 185 is of a predetermined size and location to expose the immediately previously described adjusting and locking means. To maintain the light tight integrity of case 20, when adjustment of the lens holders 144 and 147 is not desired, each threaded aperture 185 is provided with a mating threadedly engagable cap 187.

First, second, and third filters are held by the filter holders 144, 145 and 147, respectively. In each assembly the filter is held in the respective aperture 155 by a cementious material or other means known to those skilled in the art.

Consistent with an objective function of the instant invention, first filter 190 is chosen to be of a type having a light intensity transmission of approximately fifty percent and centered upon a selected Fraunhofer Line with a bandwidth of ten Angstroms at forty-five degrees angle of incidence. Third filter 193 is of a generally similar type, being centered at approximately ten Angstroms from the selected Fraunhofer Line.

Second filter 192 is chosen to have a minimum transmission of approximately forty percent and centered on the selected Fraunhofer Line with a four Angstrom bandwidth at five degrees incidence. The material of fabrication should yield a maximum shift of approximately ten Angstroms over a five degree centigrade change in temperature. A representative material is magnesium fluoride.

For each of the foregoing filters, the given data will be sufficient for the production of the desired filter by one skilled in the art of lens and filter making.

The first filter 190 and third filter 193 are angularly adjustable and lockable at the selected angular position relative the axis of the respective light ray. Second filter 192 is tunable by the operator during use for selective angular adjustment relative the optical path of the light ray extending along the axis A.

As seen in FIGS. 5 and 6, filter holder 145 is angularly pivotal about the axis of pin 164 in a rearward first direction as designated by the arrowed line K and in a reciprocal forward second direction represented by the arrowed line L. Pin 200, projecting upwardly from base plate 132, limits the angular disposition of filter holder 145 in the direction indicated by the arrowed line K. Spring holder 202 is secured to top surface 138 of base 132 at a location spaced from pin 200 in a direction generally indicated by the arrowed line L. Compression spring 203, projecting from holder 202, bears against holder 145 normally biasing same in the direction of arrowed line K against stop 200.

Tuning means for selective angular adjustment of second filter 192 is best described with reference to FIGS. 1 and 2. Adjustment means 204, projecting rearwardly from case 20, is carried proximate the right edge 37 of real panel 33. Rod 205, extending along an axis substantially parallel to the axis represented by the broken line A, extends through aperture 207 in second panel 62 and terminates with end 208, which contactingly abuts filter holder 145 proximate edge 152.

Adjusting means 204 may be readily fabricated from a conventional micrometer head, having barrel 209 and rotatably mounted thimble 210. Barrel 209 is stationarily affixed to panel 33. Thimble 210 is alternately movable in directions indicated by the arrowed line M and N. In accordance with conventional practice, rotation of thimble 210, in a clockwise direction, results in advancement in the direction of arrowed line M, while counter-rotation yields retraction in the direction of arrowed line N. Calibration indicia 212, cooperating between barrel 209 and 210, mictrometrically indicates the relative movement.

Rod 205 is an extensible element moving in extending and retracting directions in response to rotation of thimble 210. Spring 203 reinforces and maintains contact between filter holder 145 and the free end 208 of rod 205. In response to extension of rod 205 in the direction indicated by the arrowed line M, spring 203 is tensioned. In response to retraction of rod 205, in the direction of arrowed line N, spring 203 is relaxed.

In accordance with the foregoing description, it is apparent that a plurality of filter tray assemblies 130 can be made to be interchangeably and replaceably positioned within compartment 58. The tuning means described above insure that each filter 192 can be angularly adjusted to a previously calibrated position. A prior recording of a read-out of the calibration indicia 212 will provide a ready reference for repositioning any given filter.

Optical filter 72 blocks all light having a wavelength lesser than that of visible light. Similarly, optical filter 75 blocks all light having a wavelength greater than that of visible light.

Those skilled in the electronic arts will understand that it is a straightforward matter to simply employ a meter to measure the respective voltage outputs from the photovoltaic sensors 82, 83 to obtain the readings from which the calculations for determining luminescence of the target may be carried out as set forth in previously mentioned U.S. Pat. No. 3,598,994 and the literature covering the U.S.G.S. Fraunhofer Line Discriminator. However, it is desireable to somewhat automate the measuring process to assist the operator and increase the efficiency of operation.

It has thus been found that the field operation of the instrument can be substantially facilitated by employing a simple microcomputer, such as the Octagon SYS-1 (not shown), in conjunction with a commercially available low level amplifier such as the Burr Brown PGA 100B and a commercially available analog-to-digital converter module such as the Intersil 1CL7109. The Octagon SYS-1 uses a National 8073 microprocessor which features on-board TINY BASIC, a very straightforward language for performing the necessary data manipulations and calculations which result in the direct readout of the signals sensed by the photovoltaic sensors 82, 83 on a digital display 300 which may be, for example, a type PCIM200 manufactured by Printed Circuits International.

Power for the electronics (which, while not shown in detail, are represented in FIG. 2 by the printed circuit board 220 plugged into socket 221) is preferably obtained from a separately housed rechargeable battery pack (not shown) providing 12 volts to the on-board power supply 222 which simply regulates the raw voltage to the close tolerance 5 volts standard required by the digital electronic circuits and, if different, to regulated split or single-ended supply voltages appropriate to the selected analog electronic circuits.

Selecting the information to be displayed on the readout 300 may be readily accomplished by a knob 302 coupled to a switch (not shown) which selectively connects the terminals of light sensitive sensors 82, 83 (and other sensors, such as temperature, which might be desired) to the analog-to-digital converter module.

The electronics package, while entirely optional, significantly increases the efficiency and flexibility of the instrument and is preferably incorporated into the instrument.

Having fully described and disclosed the present invention in such clear and concise terms as to enable those skilled in the art to understand and practice the same, the invention claimed is:

1. In an apparatus for receiving a ray of light, which ray of light moves along an optical path having a longitudinal axis, and which apparatus includes a body and an optical device for intercepting said ray of light, improvements therein for affixing said optical device to said body at selective angular orientations relative to said longitudinal axis of said ray of light, said improvement comprising adjusting means for moving said optical device to rotate about an axis of rotation disposed substantially perpendicular to said ray of light to selective angular positions relative to said longitudinal axis of said ray of light, said adjusting means including:
   a camming surface defined by a pair of spaced-apart subsurfaces carried by said optical device for receiving a cam therebetween;
   a driver receivable in said body for rotation about an axis of rotation of said driver substantially parallel to the axis of rotation of said optical device;
   a cam carried by said driver for engagement with said camming surface for urging movement of said optical device;
   means for rotating said driver for effecting movement of said optical device; and
   locking means for selectively retaining said optical device in a selected one of said selective angular orientations.

2. The improvements of claim 1, wherein said cam is generally cylindrical about an axis parallel to and offset from the axis of rotation of said driver.

3. In an apparatus for receiving a ray of light, which ray of light moves along an optical path having a longitudinal axis, and which apparatus includes a body and an optical device for intercepting said ray of light, improvements therein for affixing said optical device to said body at selective angular orientations relative to said longitudinal axis of said ray of light, said improvements comprising adjusting means for moving said optical device to rotate about an axis of rotation disposed substantially perpendicular to said ray of light to selective angular positions relative to said longitudinal axis of said ray of light, said adjusting means including:
- a camming surface on said optical device;
- a driver receivable in said body for rotation about an axis of rotation of said driver substantially parallel to the axis of rotation of said optical device;
- a cam carried by said driver for engagement with said camming surface for urging movement of said optical device;
- means for rotating said driver for effecting movement of said optical device; and
- locking means for selectively retaining said optical device in a selected one of said selective angular orientations including an opening extending through said body in a direction substantially parallel to the axis of rotation of said driver and a fastening element extending through said opening for clamping said optical device to said body.

4. The improvement of claim 3, wherein said opening is elongated in a direction transverse to said camming surface.

5. In an apparatus for receiving a ray of light, which ray of light moves along an optical path having a longitudinal axis, and which apparatus includes a body and an optical device for intercepting said ray of light, improvements therein for affixing said optical device with respect to said body at selected angular orientations relative to said longitudinal axis of said ray of light, said improvements comprising adjusting means for moving said optical device to rotate about an axis of rotation disposed substantially perpendicular to said ray of light to selective angular positions relative to said longitudinal axis of said ray of light, said adjusting means including;
- a camming surface on said optical device;
- means defining an opening in said body for receiving driver means for engagement with said camming surface for rotation of said driver means about an axis substantially parallel to the axis of rotation of said optical device;
- driver means insertable in said opening and including a cam engageable with said camming surface for urging movement of said optical device, said driver means being removable from said opening after effecting movement of said optical device;
- locking means for selectively retaining said optical device in a selected one of said selective angular orientations; and
- cover means removably securable to said body for covering said opening to prevent leakage of light into said body when said driver means has been removed from said opening.

* * * * *